(12) United States Patent
Adams

(10) Patent No.: US 6,879,858 B1
(45) Date of Patent: Apr. 12, 2005

(54) UTERINE CONTRACTION DETECTION AND INITIATION SYSTEM AND METHOD

(75) Inventor: John M. Adams, Issaquah, WA (US)

(73) Assignee: Reproductive Health Technologies, Inc., Galveston, TX (US)

( * ) Notice: Subject to any disclaimer, the term of this patent is extended or adjusted under 35 U.S.C. 154(b) by 0 days.

(21) Appl. No.: 09/199,854

(22) Filed: Nov. 25, 1998

(51) Int. Cl.⁷ .............................................. A61B 17/42
(52) U.S. Cl. ...................................................... 607/39
(58) Field of Search ........................... 607/39, 62, 138

(56) References Cited

U.S. PATENT DOCUMENTS

| | | | |
|---|---|---|---|
| 4,256,118 A | 3/1981 | Nagel | 128/733 |
| 4,308,873 A | 1/1982 | Maynard | 128/731 |
| 4,738,268 A | 4/1988 | Kipnis | |
| 5,301,680 A | 4/1994 | Rosenberg | |
| 5,397,344 A | 3/1995 | Garfield et al. | |
| 5,400,799 A | 3/1995 | Yoches et al. | |
| 5,447,526 A * | 9/1995 | Karsdon | 607/39 |
| 5,546,953 A | 8/1996 | Garfield | |
| 5,581,369 A | 12/1996 | Righter et al. | |
| 5,623,939 A | 4/1997 | Garfield | |
| 5,776,073 A | 7/1998 | Garfield et al. | |
| 5,785,664 A | 7/1998 | Rosenberg | |
| 5,791,342 A | 8/1998 | Woodard | |
| 5,964,789 A * | 10/1999 | Karsdon | 607/39 |
| 5,991,649 A | 11/1999 | Garfield et al. | |

* cited by examiner

*Primary Examiner*—Scott M. Getzow
(74) *Attorney, Agent, or Firm*—Locke Liddell & Sapp LLP

(57) ABSTRACT

A system and method for detecting for and initiating contractions of a uterus of a human patient employs a sensor for sensing electrical activity of the uterus of the patient. Data from the sensed electrical activity is stored in memory. A processor accesses the stored data for analysis. Electrical energy is applied to the uterus to initiate a uterine contraction when the analyzed data fails to satisfy predetermined detection criteria.

34 Claims, 4 Drawing Sheets

UTERINE CONTRACTION DETECTION AND INITIATION SYSTEM AND METHOD

BACKGROUND OF THE INVENTION

The present invention is generally directed to a system and method for effecting uterine contractions of an animal. The present invention is more particularly directed to such a system and method for detecting and automatically stimulating contractions of the uterus of a human.

Prolonged pregnancy, generally classified as a gestational age exceeding 42 weeks of gestation, is associated with increased perinatal morbidity and mortality. Specifically, in addition to the increased neonatal deaths, there is an increase in the meconium aspiration, depressed infant at five minutes, and cesarean section rate. The mortality from meconium aspiration can be as high as 38% for those women managed expectantly.

Electrical energy applied to the myometrium or uterine muscle has been proposed to affect uterine contractions. One system and method to this end is disclosed in Karsdon, U.S. Pat. Nos. 5,447,526 and 5,713,940 which are incorporated herein by reference. In accordance with a preferred embodiment disclosed in these patents, a first or positive electrode is placed in surface contact to a woman's abdomen over the top of the uterus. Four negative electrodes are placed in spaced apart relation in surface contact to the woman's abdomen over lower portions of the uterus beginning at approximately a mid portion of the uterus. The negative electrodes and the positive electrode are then connected to a muscle controller which generates square wave pulse trains of current between the positive electrode and the negative electrodes. The muscle controller is capable of providing current pulse trains of selectable polarity. The controller is activated to inhibit uterine contractions when they are undesirably present or to initiate uterine contractions when they are undesirably absent.

In accordance with a further embodiment disclosed in the above-referenced Karsdon patents, a uterine contraction monitor is added to the system with feedback to the controller. The monitor is disposed for surface contact with the abdomen. The amount of electrical energy applied is thus responsive to the sensed contractions. The feedback may be negative or positive depending upon whether contraction initiation or inhibition is desired.

While the contraction monitor of Karsdon represents a significant step forward in the prenatal management of patients, there remains substantial room for improvement. The contraction monitor disclosed in the Karsdon patents is a surface monitor. Such monitors respond to physical movement.

As a result, physical movement which is a certainty to occur other than that of real contractions will also be sensed and create a noisy signal environment in which the contraction affecting device must respond. It would be most advantageous to have a contraction monitor which is substantially more specific in detecting uterine contractions.

Further, surface monitors must be worn in order to function. Hence, if a patient is to be constantly monitored, the monitor must be worn at all times. This would include times of sleep and other times when such use would either be inconvenient, cumbersome, or confining.

In addition, there is no guarantee that such a surface monitor will remain in the same place or that if removed, it will be returned to the same location on the body at a later time. This can result in signals which are variable in amplitude and other characteristics making the application of threshold criterion difficult.

Hence, there is a need in the art for an improved uterine contraction detection and stimulation system to initiate uterine contractions. More specifically, such a system must be capable of providing detection signals of good quality, in a low noise environment, and specific to uterine contractions. This would assure that stimulation to initiate uterine contractions will be provided when actually needed and not be provided when such stimulation is not required. The present invention provides such an improved uterine contraction detection and stimulation system.

SUMMARY OF THE INVENTION

The invention therefore provides a method of detecting for uterine contractions and stimulating a uterus of an animal having a body to initiate uterine contractions when uterine contractions are absent. The method includes the steps of placing first and second electrodes in contact with the body, the first electrode being placed in direct contact with the uterus, sensing electrical activity between the first and second electrodes, detecting for uterine contractions from the sensed electrical activity, and providing electrical current flow between the first and second electrodes when uterine contractions are undetected.

The invention further provides a system for detecting for uterine contractions and stimulating a uterus of an animal having a body to initiate uterine contractions when uterine contractions are absent. The system includes a first electrode, a first anchor for anchoring the first electrode to the uterus of the animal, and return current path establishing means for establishing a return current path within the body, the return current path including the first electrode. The system further includes a sense amplifier coupled to the first electrode for sensing electrical activity of the body, a detector coupled to the sense amplifier for detecting for contractions of the uterus from the sensed electrical activity and a source of electrical energy coupled to the first electrode and responsive to the detector failing to detect uterine contractions for providing electrical energy to the body along the return current path for initiating contractions of the uterus.

The invention still further provides a system for detecting for uterine contractions and stimulating a uterus of an animal having a body to initiate uterine contractions when uterine contractions are absent wherein the system includes first and second electrodes for establishing a return current path within the body, an anchor for releasably anchoring at least one of the electrodes to the uterus of the animal, a detector coupled to the first and second electrodes for detecting for uterine contractions, and a source of electrical energy responsive to the detector failing to detect uterine contractions for applying electrical energy to the first and second electrodes for initiating contractions of the uterus.

The present invention further provides a system for detecting for uterine contractions and stimulating a uterus of an animal to initiate contractions when uterine contractions are absent, the system including a sensor for sensing electrical activity of the uterus, a processor for analyzing the electrical activity of the uterus, and an energy source for applying electrical energy to the uterus responsive to the processor when the electrical activity of the uterus fails to satisfy predetermined detection criteria.

The invention further provides a system for detecting for uterine contractions and stimulating a uterus of an animal to initiate contractions when uterine contractions are absent, the system including a sensor for sensing electrical activity of the uterus, means for storing data associated with the sensed electrical activity of the uterus, a processor for analyzing the stored data, and an energy source for applying electrical energy to the uterus to initiate contractions of the uterus responsive to the processor when the analyzed data fails to satisfy predetermined detection criteria.

The invention further provides a method of detecting for uterine contractions and stimulating a uterus of an animal to initiate uterine contractions when uterine contractions are absent. The method includes the steps of sensing electrical activity of the uterus, analyzing the electrical activity of the uterus, and applying electrical energy to the uterus to initiate contractions of the uterus when the analyzed electrical activity of the uterus fails to satisfy predetermined detection criteria.

The invention still further provides a method of detecting for uterine contractions and stimulating a uterus of an animal to initiate uterine contractions, wherein the method includes the steps of sensing electrical activity of the uterus, generating data associated with the sensed electrical activity, storing the data associated with the sensed electrical activity; analyzing the stored data, and applying electrical energy to the uterus to initiate contractions of the uterus responsive to the analyzed data failing to satisfy predetermined detection criteria.

BRIEF DESCRIPTION OF THE DRAWINGS

The features of the present invention which are believed to be novel are set forth with particularity in the appended claims. The invention, together with further objects and advantages thereof may best be understood by making reference to the following description taken in conjunction with the accompanying drawings, in the several figures of which like reference numerals identify identical elements, and wherein:

DETAILED DESCRIPTION

Figure 1:
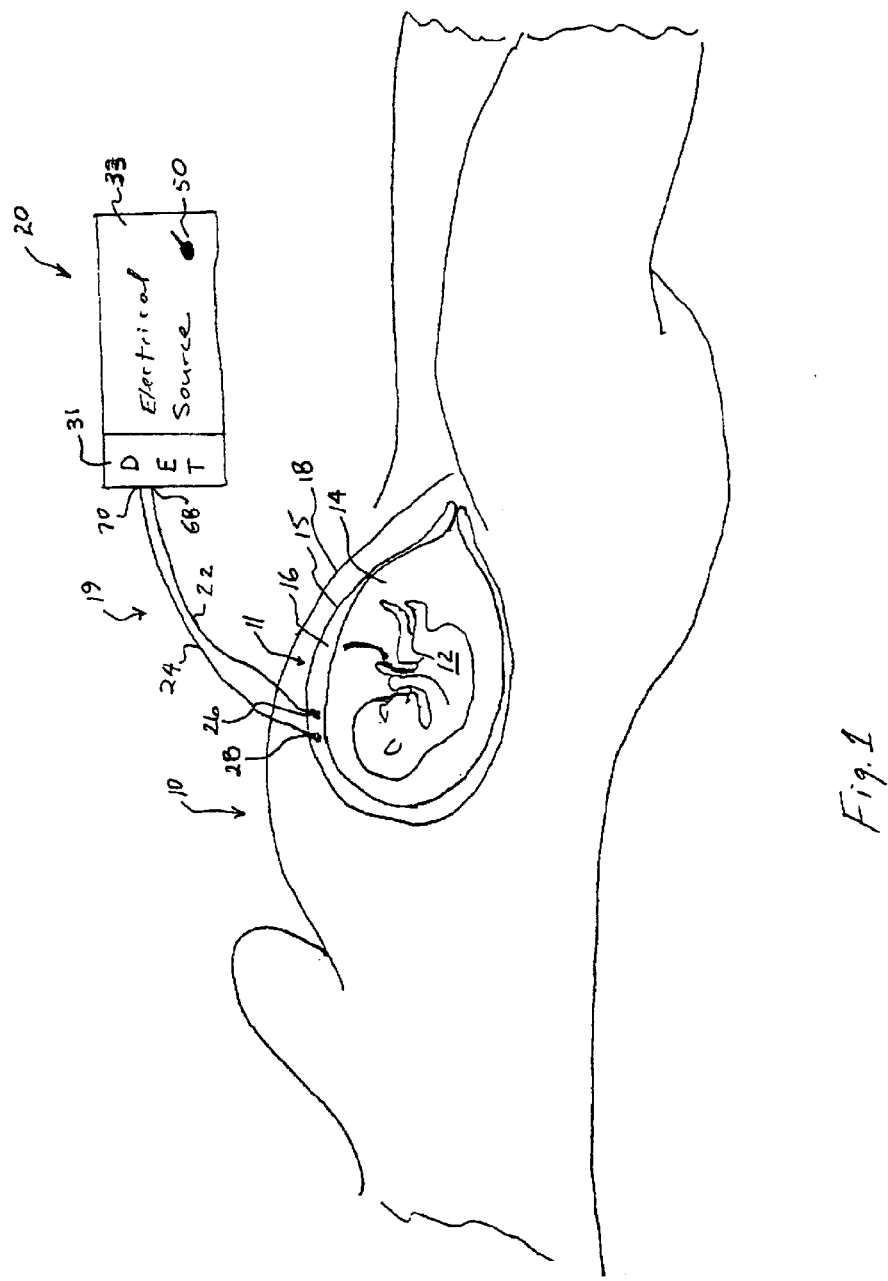
FIG. 1 is a side view, partly cut away, of a pregnant patient and a system for detecting and initiating uterine contractions having a pair of electrodes in direct contact with the patient's uterus in accordance with a preferred embodiment of the present invention.

Referring now to FIG. 1, it schematically illustrates a pregnant patient 10 having a uterus 11 and a fetus 12 disposed within the uterus 11. The uterus 11 is enclosed by the abdominal wall 18 of the patient and includes an amniotic cavity 14 which is defined by the uterine wall 15. The uterine wall 15 is primarily comprised of the uterine muscle or myometrium 16. As is well known, the fetus 12 is disposed within amniotic fluid contained within the amniotic cavity 14.

In accordance with the present invention, a system 19 detects for and initiates contractions of the uterus 11. More specifically, the system 19 includes a detection and initiation unit 20 including a uterine contraction detector 31 and a source of electrical energy 33. The system 19 further includes first and second leads 22 and 24 having first and second electrodes 26 and 28 respectively. The first and second electrodes are coupled directly to the uterus 11 to establish a current return path between the electrodes within the myometrium 16. As will be seen with respect to FIG. 2, the electrodes 26 and 28 are coupled to both the detector 31 and energy source 33 of unit 20.

As can be clearly seen in FIG. 1, the electrodes 26 and 28 of leads 22 and 24 respectively are in direct contact with the myometrium 16. The electrodes 26 and 28 are also preferably configured so as to be releasably anchored within the myometrium 16 as will be more particularly described subsequently.

In the detection of contractions of the uterus 11, the electrodes 26 and 28 provide an electromyographic signal (EMG) representing the electrical activity of the myometrium 16. Because the electrodes 26 and 28 are within the myometrium 16, the EMG is very specific to the electrical activity of the myometrium 16. When the EMG satisfies a predetermined criteria to be explained subsequently, uterine contractions are determined to be present. Conversely, when the EMG fails to satisfy a predetermined criteria, uterine contractions are considered to be sufficiently absent to require uterine stimulation for uterine contraction initiation.

When contractions of the uterus 11 are to be initiated, the electrical energy source 33 is activated by the detector 31 to provide, for example, trains of square wave voltage pulses. The electrical energy is applied directly to the myometrium 16 along the aforementioned current return path within the myometrium by virtue of the electrodes 26 and 28 being directly in contact with the myometrium 16. Because the electrodes 26 and 28 are fixedly anchored within the myometrium 16, they will not be dislodged by the uterine contractions to enable the therapy to have its complete therapeutic effect. However, because the electrodes are releasably anchored, they may be readily removed in a noninvasive manner when no longer needed.

To lend further understanding of the present invention, the electrical activity of the uterus can exhibit two distinct forms of activity. One form is that of a uterine contracture which is exhibited long before actual labor. Contractures are represented by bursts of electrical activity which can last on the order of several minutes and which are widely spaced apart by separations of about an hour or more. Contractures are disorganized muscle activity of the myometrium causing minimal, if any, physical manifestations of the myometrium.

The other form is that of a uterine contraction. Contractions are represented by relatively short bursts of electrical energy with the bursts being relatively closely spaced apart. For example, during labor, the uterine contraction electrical bursts of energy may have durations of thirty seconds or less with separations on the order of twenty minutes or less. Contractions, as compared to contractures, are organized muscle activity of the myometrium causing pronounced physical manifestations of the myometrium. It is the occurrence of contractions that is most identified as labor.

The electrical energy bursts of both contractures and contractions are made up of electrical waves having separations of, for example, three hundred milliseconds to nine hundred milliseconds (300 ms to 900 ms). As will be seen subsequently, one or more characteristics of the EMG electrical bursts are used to identify actual contractions or the lack thereof in need of initiation.

Figure 2:
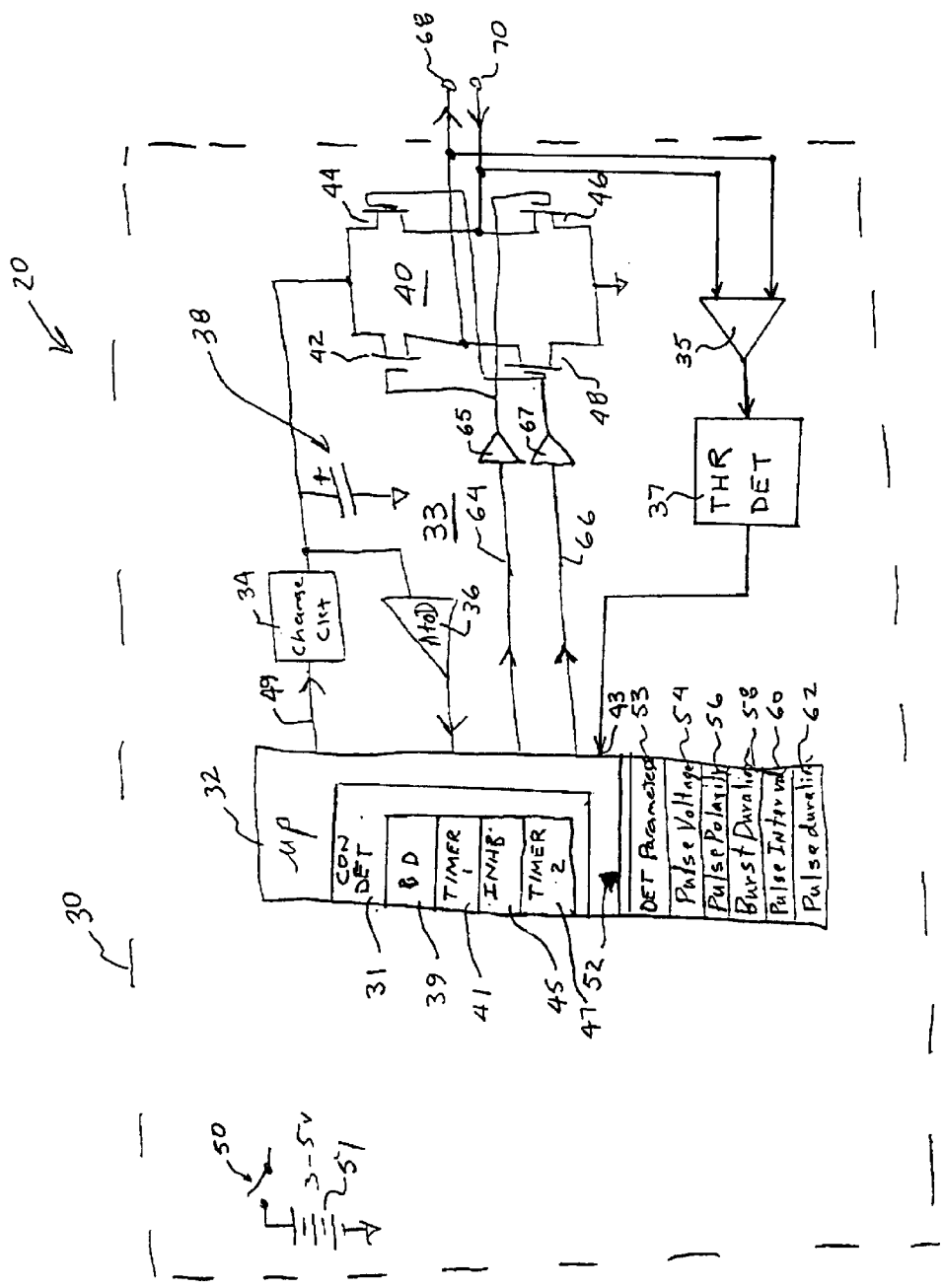
FIG. 2 is a schematic diagram of a uterine contraction detection and initiation unit embodying further features of the present invention.

Referring now to FIG. 2, it illustrates in schematic form, the uterine contraction detection and initiation unit 20 of FIG. 1. The unit 20 includes the contractions detector 31 and energy source 33 within an enclosure 30. The unit 20 is turned on by a switch 50 which connects a battery 51 to the various components of the unit 20 when contractions are to be initiated or maintained.

Within the enclosure 30 is also a microprocessor 32 which, in a manner well known in the microprocessor art, operates on operating instructions stored in an internal memory 52 or an external memory (not shown). As a result of such operation, the microprocessor 32 implements the contractions detector 31 including burst duration stage 39, a first timer 41, an inhibit stage 45 and a second timer 47. Also, stored in memory portion 53 of memory 52, are preprogrammed contraction detection parameters or criteria.

The contraction detector 31 further utilizes a sense amplifier 35 and a threshold circuit 37. The sense amplifier 35 has a pair of inputs which are coupled to outputs 68 and 70 of the unit 20. The outputs 68 and 70 are adapted to be coupled to the first and second electrodes 26 and 28.

The electrodes 26 and 28 provide the EMG representing the electrical activity of the myometrium. The EMG is amplified by the sense amplifier 35. The amplified EMG is then provided by the sense amplifier 35 to the threshold detector 37. Whenever an electrical wave from the sense amplifier 35 exceeds a threshold magnitude set by the threshold detector 37, the threshold detector will provide an output to an interrupt input 43 of the microprocessor 32.

The burst duration stage 39 time stamps each interrupt input and stores each time stamp in memory 52. It also, with timer 41, starts keeping time from each interrupt input. When the timer 45 has timed a predetermined time period of, for example, five seconds without being reset by another interrupt, the burst duration stage 39 considers the current burst to be completed. The next interrupt will then represent the beginning of the next burst of electrical activity.

The inhibit stage 45 precludes the energy source 33 from stimulating the uterus as long as contractions are sufficiently present. To that end, the second timer 47 starts keeping time from the beginning of each burst as determined by the duration stage 39. As long as the second timer 47 is reset by the burst duration stage 39 before it times out, the inhibit stage 45 will continue to inhibit the energy source 33. However, when a next burst fails to begin within the time out time period of the second timer 47, the inhibit stage 45 activates the energy source 33 for stimulating the uterus to initiate the next contraction. The time out period of timer 47 may be, for example, on the order of two minutes. As a result, if a next burst does not occur within two minutes of its immediately preceding burst, the beginning the contraction detector 31 will consider the contractions to be insufficient and warranting uterine stimulation to initiate the next uterine contraction. Hence, a new contraction will be initiated when a uterine contraction is undetected within a predetermined time from the beginning of an immediately preceding uterine contraction. As can be appreciated by those skilled in the art, the time out period may be tailored to an individual patient. The above time out period is provided as being exemplary only.

The energy source 33 includes a charging circuit 34, an analog to digital converter 36, a storage capacitor 38, and an H bridge 40 comprising field effect transistors 42, 44, 46, and 48.

The electrical energy source 33 is activated by the inhibit stage 45 of the contractions detector 31 over a line 49 which causes the charge circuit 34 to charge capacitor 38. The memory 52 has storage locations 54, 56, 58, 60, and 62 for storing preprogrammed energy delivery parameters such as pulse voltage, pulse polarity, burst duration, pulse interval, and pulse duration respectively. The foregoing parameters including the detection parameters may be stored in the memory 52 with a programming computer (not shown) of the type well known in the art.

The charge circuit 34 charges the storage capacitor 38 to the pulse voltage programmed at memory location 54. The output of the charge circuit 34 is monitored by the analog to digital connector 36 which provides the microprocessor with a digital representation of the output voltage of the charge circuit 34. In this manner, the microprocessor is capable of regulating or controlling the charge circuit 34 to maintain the preprogrammed pulse voltage across the capacitor 38.

The H bridge 40 is of the type well known in the art which is controlled by the microprocessor 32 over control lines 64 and 66 which are provided with buffers 65 and 67 respectively to accommodate required voltage swings and higher voltage applied to H bridge 40. The signals provided by the microprocessor over the control lines 64 and 66 cause the energy source 33 to provide a train of output pulses at the output terminals 68 and 70 having the pulse polarity, burst duration, pulse interval, and pulse duration as preprogrammed in memory locations 56, 58, 60 and 62 respectively of the memory 52. The output terminals 68 and 70 of the unit 20 are coupled to the leads 22 and 24 respectively as shown in FIG. 1 to provide the electrodes 26 and 28 with the preprogrammed electrical energy.

Figure 3:
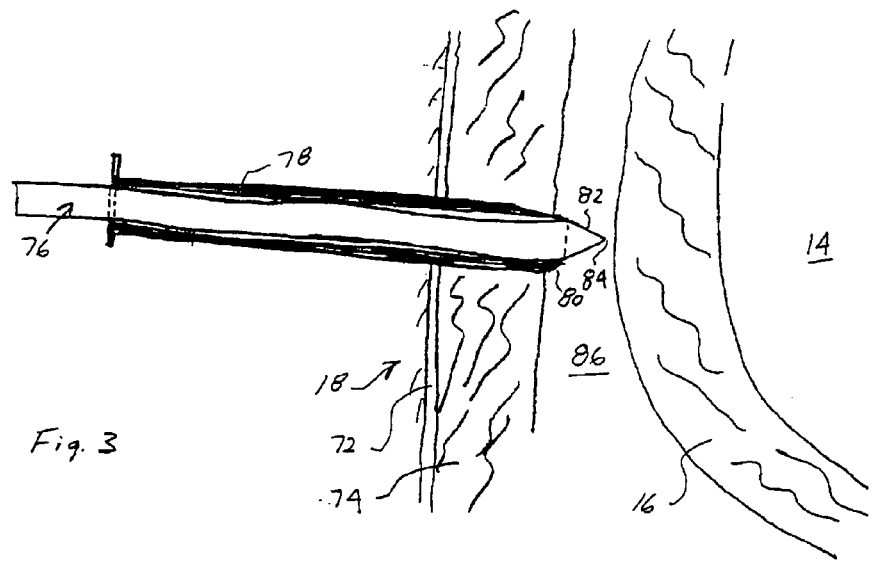
FIG. 3 is a partial side view to an enlarged scale and partly in cross section illustrating a first step in placing an electrode in direct contact with a uterus of a patient.
Figure 4:
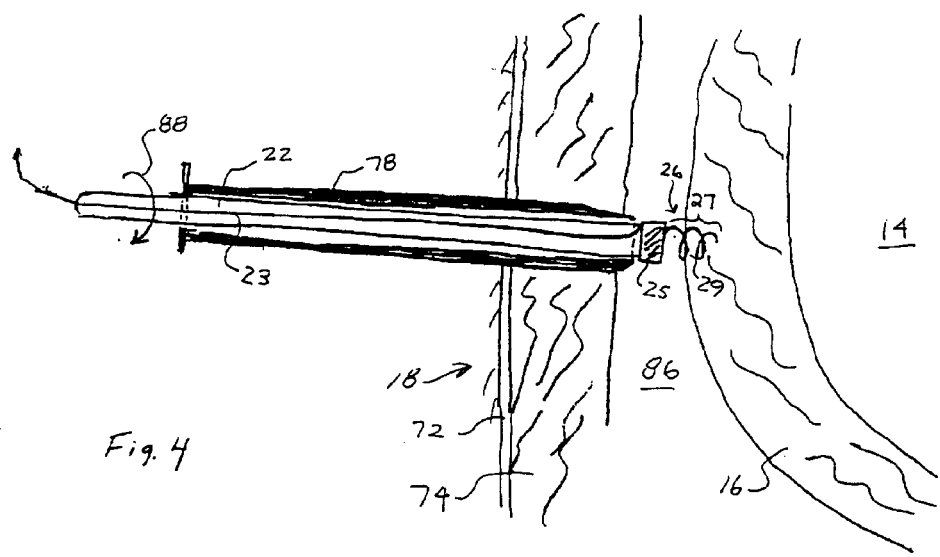
FIG. 4 is a partial side view to an enlarged scale and partly in cross-section illustrating a further step in placing an electrode in direct contact with a uterus of a patient.
Figure 5:
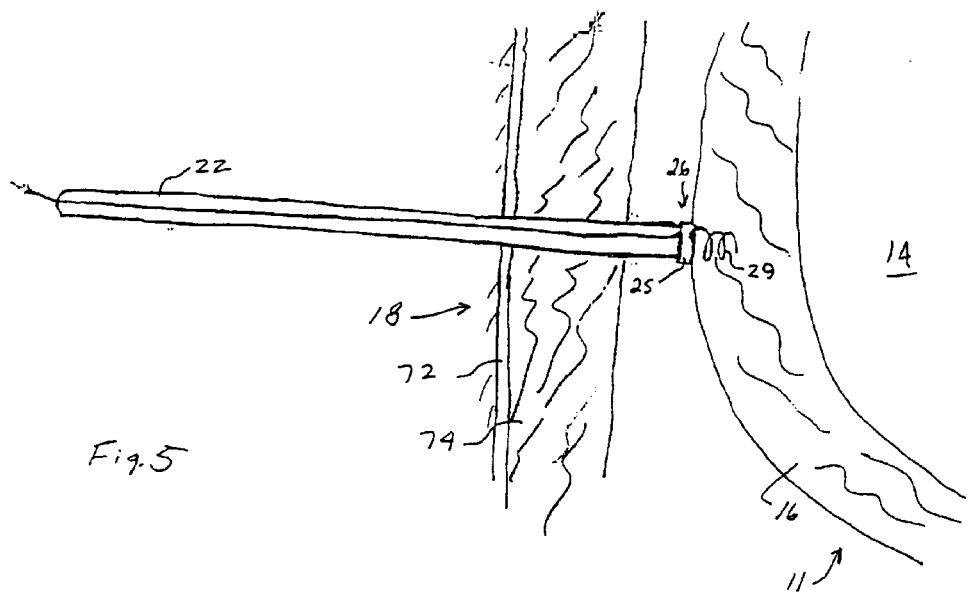
FIG. 5 is a partial side view to an enlarged scale and partly in cross-section illustrating an electrode in direct contact with the uterus of a patient in accordance with a preferred embodiment of the present invention.

FIGS. 3–5 illustrate a manner in which the electrodes 26 and 28 may be substantially non-invasively placed in direct contact with the uterus 11 through the abdomen 18 and more particularly in direct contact with the myometrium 16 in accordance with a preferred embodiment of the present invention. Referring first to FIG. 3, there is illustrated, to an enlarged scale, the abdominal wall 18 and the myometrium 16. The abdominal wall includes the skin 72 and the abdominal muscle 74.

In an initial step, a removable inner needle 76 is first inserted into an introducer tube 78. The introducer tube 78 terminates in a conical surface 80 which matches the terminating conical surface 82 of the removable inner needle 76. With the conical surfaces 82 and 80 aligned as shown in FIG. 3, the introducer tube 78 and removable inner needle 76 are moved in unison to pierce the skin 72 and abdominal muscle 74. Movement of the introducer tube 78 and removable inner needle 76 is terminated when the tip 84 of the needle 76 has entered the space 86 between the abdominal muscle 74 and myometrium 16 to such an extent that the conical surface 80 of the introducer tube 78 is within the space 86. Once the removable inner needle 76 and introducer tube 78 are positioned as shown in FIG. 3, the removable inner needle 76 is withdrawn from the introducer tube 78. With the removable inner needle 76 thus removed from the introducer tube 78, the introducer tube 78 is now ready to receive the electrode 26 at the distal end of its lead 22 as illustrated in FIG. 4.

The lead 22 has a cylindrical lead body with an inner electrical conductor 23 which contacts a conductive collar 25 of the electrode 26. The electrode 26 has a structure 27 secured to the collar 25 by welding, for example. The structure 27 is formed of a relatively rigid conductive wire 29 configured as a screw-in tip. More specifically, the electrode structure 27 is formed in the shape of a helix so that when the lead 22 is introduced through the introducer tube 78 to an extent permitting the electrode 26 to contact the myometrium 16, rotation of the lead 22 as indicated by the arrow 88 causes the helical screw-in tip 29 of electrode 26 to screw into the myometrium 16.

When the lead 22 has been rotated a sufficient number of turns to fully embed the electrode tip 29 within the myometrium 16, the lead will be securely, but releasably, anchored within the myometrium 16. This is illustrated in FIG. 5 where it can be seen that the helical tip 29 of the electrode 26 is fully embedded within the myometrium 16. Once this is accomplished, the introducer tube 78 may be removed to thus render the lead 22 passing through the abdominal wall 18 including the skin 72 and abdominal muscle 74 with the electrode 26 securely anchored to the uterus 11 and more specifically, the myometrium 16. As a result, during the therapy of initiating contractions of the uterus 11, the contractions of the uterus 11 will not dislodge the electrode 26 from the myometrium 16. However, when therapy is no longer required and the electrode 26 is no longer needed, it may be readily withdrawn by just rotating the lead 22 in a direction opposite that shown at 88 in FIG. 4 and pulling the lead from the patient when the tip 29 is disengaged from the myometrium.

Figure 6:
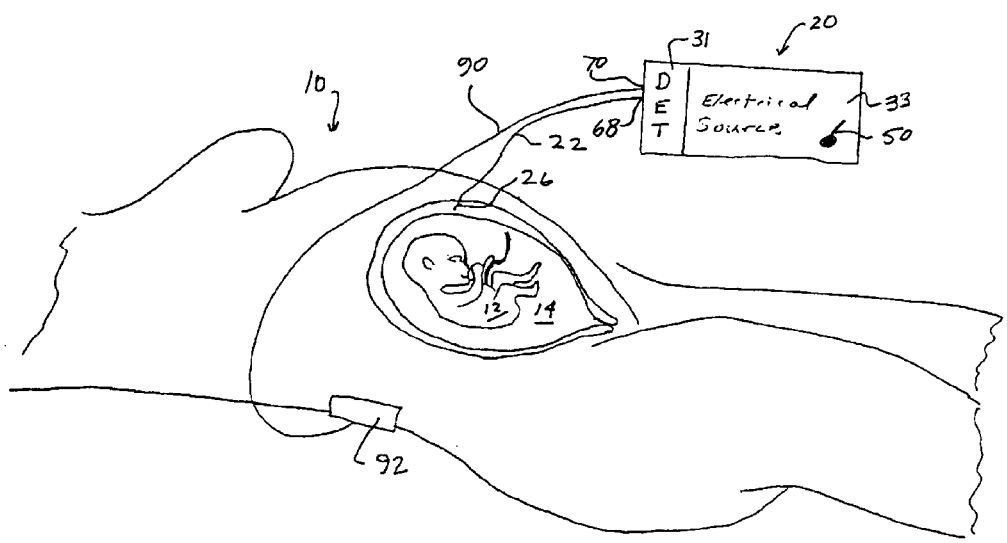
FIG. 6 is a side view, partly cut away of a pregnant patient and another uterine contraction detection and initiation system embodying the present invention.

Referring now to FIG. 6, it illustrates a further embodiment of the present invention. Here it may be seen that the unit 20 is coupled directly to the myometrium through the lead 22 and electrode 26 as previously described while another lead 90 couples the unit 20 to a surface of the body of the patient 10 with a surface or patch electrode 92. The patch or surface electrode 92 is in surface contact with a posterior portion of the body of the patient 10 and more specifically, on the back of the patient. With such an arrangement, a return current path is established between the electrodes 26 and 90. The electrical energy from the energy source 33 of the unit 20 will remain concentrated in the myometrium given the large surface area of electrode 92 compared to electrode 26. The fetus 12 and the body of the patient 10 will only be exposed to dispersed energy which will be well within safe limits for both the fetus 12 and mother 10.

While particular embodiments of the present invention have been shown and described, modifications may be made, and it is therefore intended to cover in the appended claims all such changes and modification which fall within the true spirit and scope of the invention.

What is claimed is:

1. A method of detecting for uterine contractions of a uterus of an animal having a body to initiate uterine contractions when uterine contractions are absent, the method including the steps of:
    placing first and second electrodes in contact with the body, the first electrode being placed in direct contact with the uterus;
    sensing electrical activity between the first and second electrodes;
    detecting for uterine contractions from the sensed electrical activity; and
    providing electrical current flow between the first and second electrodes when uterine contractions are undetected.

2. A method as defined in claim 1 wherein the providing step is performed when a uterine contraction is undetected within a predetermined time of an immediately preceding uterine contraction.

3. A method as defined in claim 1 wherein the providing step is performed when a uterine contraction is undetected within a predetermined time from the beginning of an immediately preceding uterine contraction.

4. A method as defined in claim 1 wherein the placing step includes anchoring the first electrode to the uterus.

5. A method as defined in claim 1 wherein the placing step includes passing the first electrode through skin of the animal.

6. A method as defined in claim 1 wherein the placing step includes releasably anchoring the first electrode to the uterus.

7. A method as defined in claim 6 wherein the placing step further includes anchoring the first electrode to the myometrium.

8. A method as defined in claim 1 wherein the placing step includes contacting the second electrode with the uterus.

9. A method as defined in claim 8 wherein the contacting step further includes anchoring the second electrode to the uterus.

10. A method as defined in claim 8 wherein the contacting Step further includes passing the second electrode through skin of the body.

11. A method as defined in claim 8 wherein the contacting step further includes placing the second electrode in direct contact with the myometrium.

12. A method as defined in claim 11 wherein the contacting step further includes anchoring the second electrode to the myometrium.

13. A method as defined in claim 8 wherein the second electrode is a surface electrode and wherein the contacting step includes making surface contact between the second electrode and the body.

14. A method as defined in claim 13 wherein the contacting step further includes making surface contact between the surface electrode and a posterior portion of the body.

15. A system for detecting for uterine contractions and stimulating a uterus of an animal having a body to initiate uterine contractions when uterine contractions are absent, the system comprising:
    a first electrode;
    a first anchor for anchoring the first electrode to the uterus of the animal;
    return current path establishing means for establishing a return current path within the body, the return current path including the first electrode;
    a sense amplifier coupled to the first electrode for sensing electrical activity of the body;
    a detector coupled to the sense amplifier for detecting for contractions of the uterus from the sensed electrical activity; and
    a source of electrical energy coupled to the first electrode and responsive to the detector failing to detect uterine contractions for providing electrical energy to the body along the return current path for initiating contractions of the uterus.

16. A system as defined in claim 15 wherein the detector includes a timer for timing the time since a last uterine contraction and wherein the source is responsive to the timer timing a predetermined time period since the last uterine contraction for providing the electrical energy for initiating contractions of the uterus.

17. A system as defined in claim 15 wherein the first anchor is a releasable anchor.

18. A system as defined in claim 17 wherein the first anchor is configured for anchoring the first electrode to the myometrium.

19. A system as defined in claim 18 wherein the first anchor comprises a screw-in tip.

20. A system as defined in claim 19 wherein the screw-in tip is a helical coil.

21. A system as defined in claim 19 wherein the first electrode includes structure forming the screw-in tip.

22. A system as defined in claim 17 wherein the return current path establishing means comprises a second electrode adapted for making electrical contact with the body.

23. A system as defined in claim 22 wherein the second electrode is arranged for direct contact with the uterus.

24. A system as defined in claim 23 further including a second anchor for anchoring the second electrode to the uterus.

25. A system as defined in claim 24 wherein the second anchor is arranged for anchoring the second electrode to the myometrium.

26. A system as defined in claim 24 wherein the second anchor is a releasable anchor.

27. A system as defined in claim 26 wherein the second anchor includes a screw-in tip.

28. A system as defined in claim 26 wherein the second electrode includes structure forming the second anchor.

29. A system as defined in claim 22 wherein the second electrode is a surface electrode for making surface contact with the body.

30. A system for detecting for uterine contractions and stimulating a uterus of an animal having a body to initiate uterine contractions when uterine contractions are absent, the system comprising:
    first and second electrodes for establishing a return current path within the body;
    an anchor for releasably anchoring at least one of the electrodes to the uterus of the animal;
    a detector coupled to the first and second electrodes for detecting for uterine contractions; and
    a source of electrical energy responsive to the detector failing to detect uterine contractions for applying electrical energy to the first and second electrodes for initiating contractions of the uterus.

31. A system for detecting for uterine contractions and stimulating a uterus of an animal to initiate contractions when uterine contractions are absent, the system comprising:
    a sensor for sensing electrical activity of the uterus;
    a processor for analyzing the electrical activity of the uterus and determining an absence of uterine contractions; and
    an energy source for applying electrical energy to the uterus responsive to the processor when the electrical activity of the uterus fails to satisfy predetermined detection criteria from the absence of the uterine contractions.

32. A system for detecting for uterine contractions stimulating a uterus of an animal to initiate contractions when uterine contractions are absent, the system comprising:
    a sensor for sensing electrical activity of the uterus;
    means for storing data associated with the sensed electrical activity of the uterus;
    a processor for analyzing the stored data and determining an absence of uterine contractions; and
    an energy source for applying electrical energy to the uterus to initiate contractions of the uterus responsive to the processor when the analyzed data fails to satisfy predetermined detection criteria from the absence of the uterine contractions.

33. A method of detecting for uterine contractions and stimulating a uterus of an animal to initiate uterine contractions when uterine contractions are absent, the method including the steps of:
    sensing electrical activity of the uterus;
    analyzing the electrical activity of the uterus; and
    applying electrical energy to the uterus to initiate contractions of the uterus when the analyzed electrical activity of the uterus fails to satisfy predetermined detection criteria.

34. A method of detecting for uterine contractions and stimulating a uterus of an animal to initiate uterine contractions when uterine contractions are absent, the method including the steps of:
    sensing electrical activity of the uterus;
    generating data associated with the sensed electrical activity;
    storing the data associated with the sensed electrical activity;
    analyzing the stored data; and
    applying electrical energy to the uterus to initiate contractions of the uterus responsive to the analyzed data failing to satisfy predetermined detection criteria.

* * * * *